(12) United States Patent
Taylor et al.

(10) Patent No.: US 7,571,548 B2
(45) Date of Patent: Aug. 11, 2009

(54) CYCLING PEDAL LEG ANGLE OPTIMIZER

(76) Inventors: Joshua David Taylor, 8140 Heritage Dr., Alburtis, PA (US) 18011; Louise Hernandez Chang, 843 15th St. #3, Santa Monica, CA (US) 90403

( * ) Notice: Subject to any disclaimer, the term of this patent is extended or adjusted under 35 U.S.C. 154(b) by 80 days.

(21) Appl. No.: 11/828,671

(22) Filed: Jul. 26, 2007

(65) Prior Publication Data

US 2009/0025240 A1  Jan. 29, 2009

(51) Int. Cl.
*G01B 3/56* (2006.01)
*B43L 7/033* (2006.01)

(52) U.S. Cl. ............................... 33/512; 33/1 N; 33/482

(58) Field of Classification Search .................. 33/1 N, 33/3 R, 403, 465, 471, 482, 511, 512, 533, 33/534, 538, 613, 645, 562
See application file for complete search history.

(56) References Cited

U.S. PATENT DOCUMENTS

| 2,586,074 | A |   | 2/1952 | Memluck |   |
|---|---|---|---|---|---|
| 3,270,420 | A | * | 9/1966 | Simril | 33/471 |
| 4,603,687 | A |   | 8/1986 | Greenwood |   |
| 4,708,128 | A | * | 11/1987 | Ancillotti | 601/36 |
| 4,804,001 | A | * | 2/1989 | McLeod, Jr. | 600/595 |
| 4,930,497 | A |   | 6/1990 | Saringer |   |
| 5,007,675 | A | * | 4/1991 | Musto et al. | 297/215.14 |
| 5,263,492 | A | * | 11/1993 | Voyce | 600/595 |
| 5,801,303 | A | * | 9/1998 | Rosenquist | 73/114.77 |
| 6,336,909 | B2 | * | 1/2002 | Gildersleeve et al. | 602/26 |
| 6,470,591 | B2 | * | 10/2002 | Rutkowski | 33/832 |
| 6,823,603 | B1 | * | 11/2004 | Tindall | 33/471 |
| 6,997,470 | B2 | * | 2/2006 | Clutton | 280/287 |
| 7,047,831 | B2 | * | 5/2006 | Reynolds et al. | 73/866.4 |
| 7,293,363 | B1 | * | 11/2007 | Parker | 33/471 |
| 2007/0266579 | A1 | * | 11/2007 | Briscoe et al. | 33/503 |
| 2007/0276296 | A1 | * | 11/2007 | Bright et al. | 600/595 |
| 2008/0196263 | A1 | * | 8/2008 | Okura et al. | 33/613 |

FOREIGN PATENT DOCUMENTS

| DE | 20000170 | U1 | * | 6/2001 |
| EP | 926054 | A1 | * | 6/1999 |
| JP | 2000009401 | A | * | 1/2000 |
| RU | 2019132 | C1 | * | 9/1994 |

\* cited by examiner

*Primary Examiner*—R. A. Smith
(74) *Attorney, Agent, or Firm*—Felix L. Fischer

(57) ABSTRACT

Optimizing pedal angle for a cyclist is accomplished with a template having a central body with an aperture for positioning over the lateral condyle in a cyclist's knee. A fist alignment arm extends from the central body and incorporates an alignment indicia for positioning between the knee and hip of the cyclist. A second alignment arm extends from the central body at a predetermined angle with respect to the first alignment arm and employs an angular alignment indicia for relative placement over a malleolus bone of an ankle of the cyclist.

5 Claims, 5 Drawing Sheets

CYCLING PEDAL LEG ANGLE OPTIMIZER

BACKGROUND OF THE INVENTION

1. Field of the Invention

The present invention relates to anthropomorphic measurement devices. More particularly the present invention relates to an enhanced goniometer type measurement device for simple yet accurate measurement of knee angle of the upper and lower leg for optimizing seat height on a pedal driven device for proper leg position.

2. Description of the Related Art

The requirement for proper adjustment of seat height on bicycles and pedal driven exercise devices is well known. Improper seat height can create leg strain and potentially harmful stress effects on the knee joint by creating leg angles in the pedal rotation that are not optimized. With emphasis in current exercise physiology on low impact aerobic and cardiovascular training, activities such as Spinning® stationary cycling and indoor cycling are gaining significant popularity. However, adjustment of the exercise bike for proper seat height, particularly where numerous users employ the same device at a club or gym, is often not accomplished properly. Additionally, for bicycle riders and shops selling cycles and equipment, optimizing leg angle through proper seat positioning is critical to obtain the greatest performance for the cyclist as well as preventing injury due to the highly repetitive motion.

The importance of creating the appropriate leg angle is demonstrated by the complexity of adjustment devices for bicycles and pedal driven exercise devices in the prior art. As exemplary of this art are U.S. Pat. No. 4,708,128 entitled Stationary Bicycle with Inclinable Pedal Crank Axes for Treating Knee Anamolies issued Nov. 24, 1982, U.S. Pat. No. 5,007,675 entitles Fore-and-Aft Adjuster for Bicycle Seat issued Apr. 16, 1991 and U.S. Pat No. 6,997,470 entitles Pedaling Apparatus issued Feb. 14, 2006.

The complexity of anthropomorphic measurement devices for typical applications is shown by representative patents for prior art devices such as It is therefore desirable to provide a device for simple yet accurate and effective measurement of leg angle at the knee to easily adjust seat height on bicycles and pedal driven exercise devices.

SUMMARY OF THE INVENTION

The present invention allows optimizing pedal angle for a cyclist by providing a template with a central body having an aperture for positioning over the lateral condyle in a cyclist's knee. A first alignment arm extends from the central body and incorporates an alignment indicia for positioning between the knee and hip of the cyclist. A second alignment arm extends from the central body at a predetermined angle with respect to the first alignment arm and employs an angular alignment indicia for relative placement over a malleolus bone of an ankle of the cyclist.

In an exemplary embodiment, the first alignment arm of the template incorporates an aperture for alignment over the hip. In an alternative embodiment, the first alignment arm incorporates an aperture bisected by the alignment indicia to the hip.

To assist in positioning of the template, the central body further includes an angular indicia for positioning proximate a knee cap on the cyclist'knee and the angular alignment indicia incorporated on the second alignment arm includes a first secondary visual clues for a proper range of alignment angle for the malleolus bone and second set of secondary visual clues for improper angular alignment.

For the exemplary embodiments, the angular alignment indicia incorporated in the second alignment arm includes a range of leg angle between approximately 25° and 35° with a medial 30° line.

BRIEF DESCRIPTION OF THE DRAWINGS

These and other features and advantages of the present invention will be better understood by reference to the following detailed description when considered in connection with the accompanying drawings wherein.

DETAILED DESCRIPTION OF THE INVENTION

Figure 1:
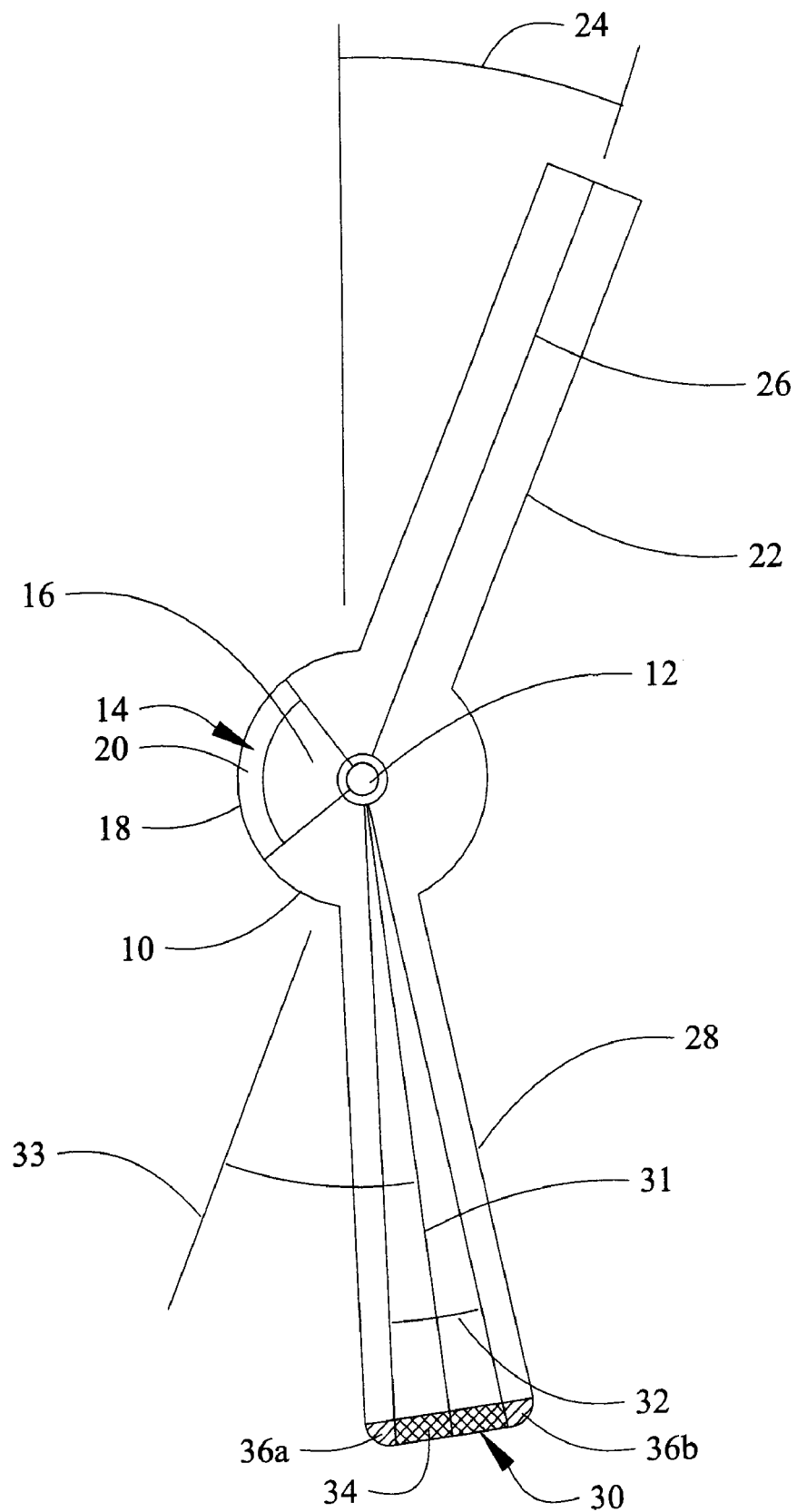
FIG. 1 is a side view of an exemplary embodiment of the present invention.
Figure 2:
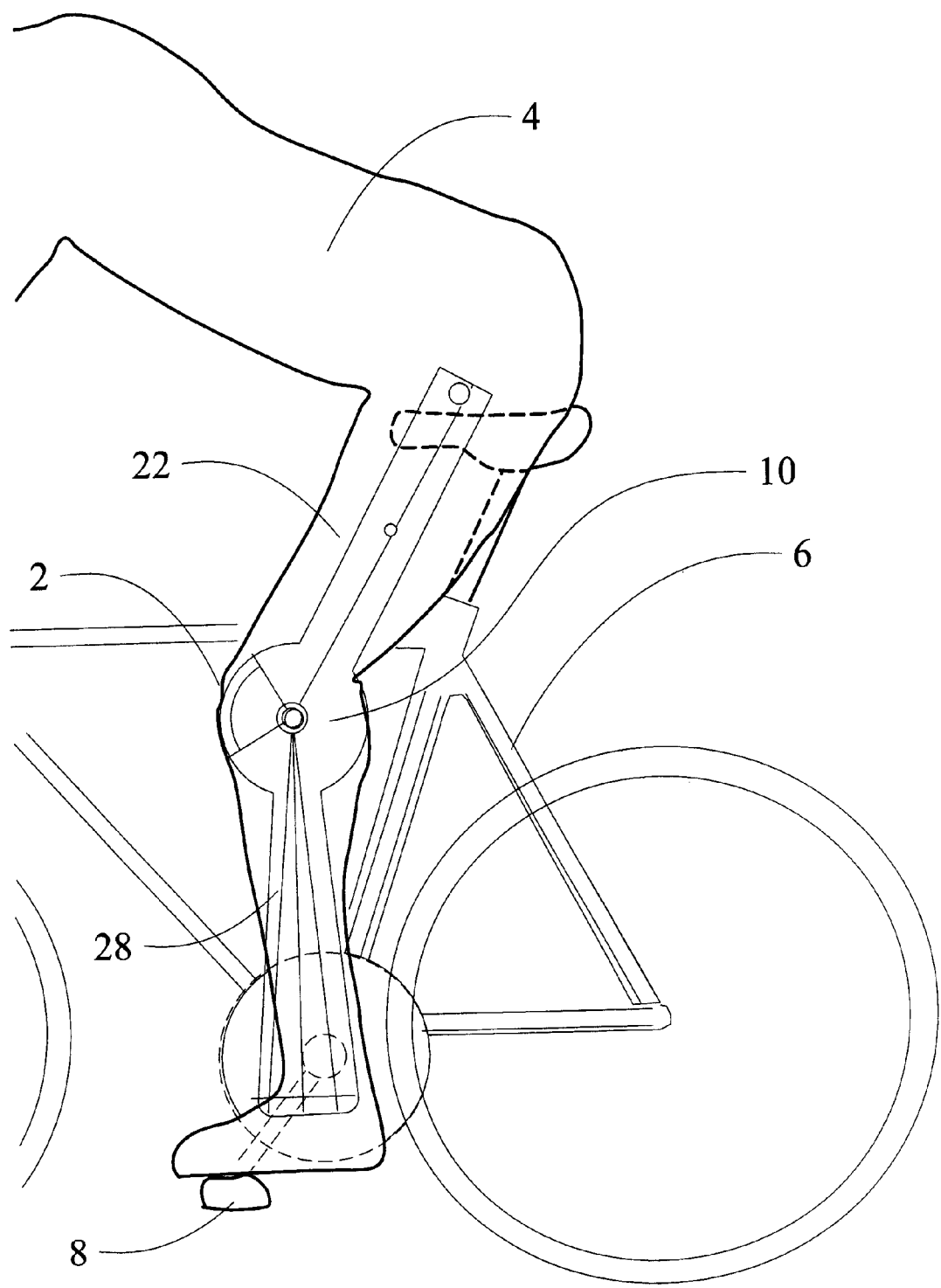
FIG. 2 is a side view of the embodiment of the invention in use for measurement of leg angle.
Figure 3:
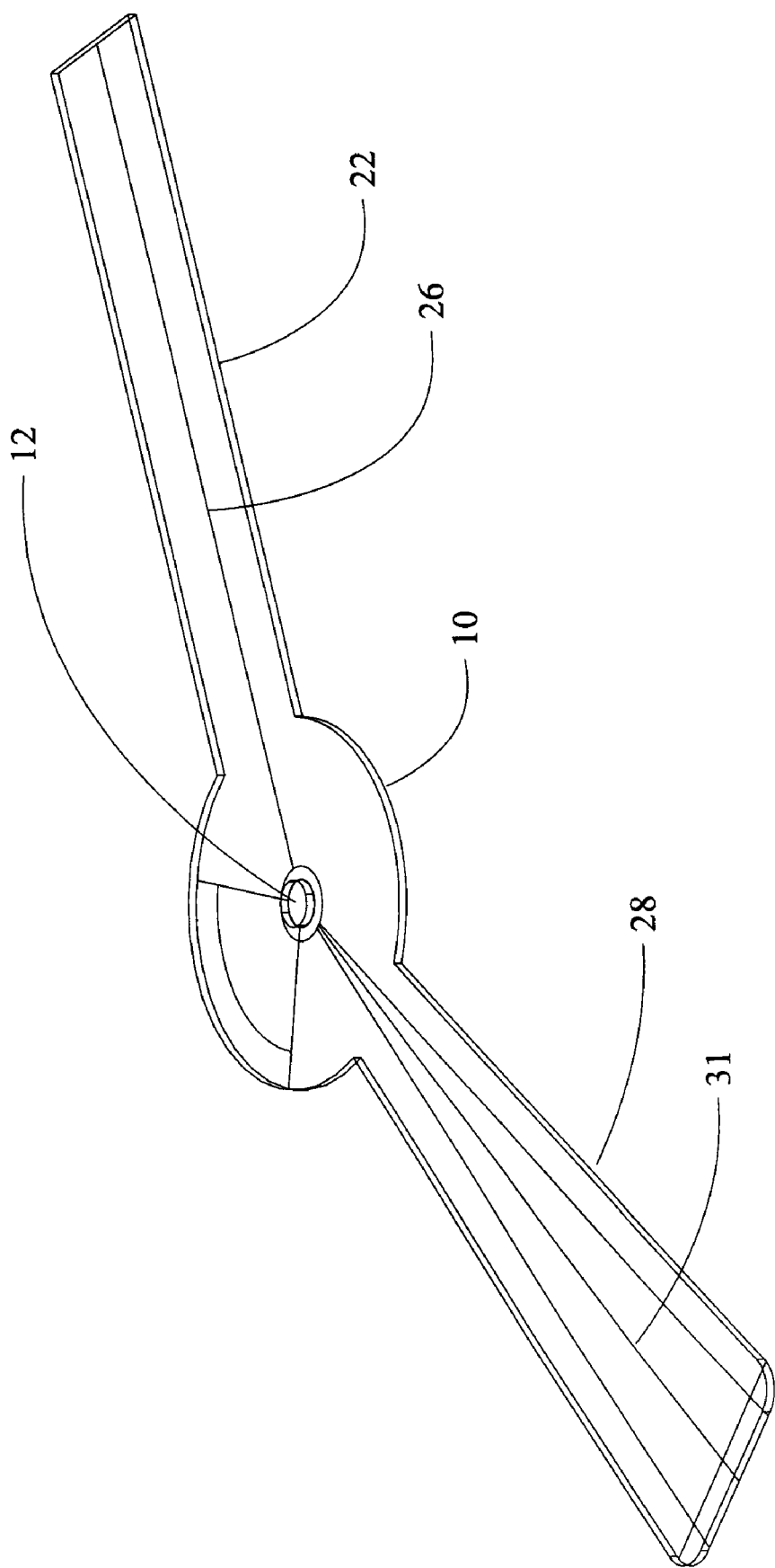
FIG. 3 is an isometric view of the embodiment of FIG. 1 with thickness exaggerated for clarity of presentation.

The embodiment of the present invention shown in FIG. 1 provides a device for accurate measurement of leg angle at the knee for a specific desired optimum range, referred to herein as the "optimizer". A central body 10, which is circular for the embodiment shown in the drawings, is employed for positioning the optimizer for the lateral side of the knee 2 of a cyclist 4 seated on a bicycle 6 or pedal exercise device with the associated foot on pedal 8 as shown in FIG. 2. An aperture 12 centrally located in the body is employed to position the optimizer by locating the aperture over the lateral condyle on the knee. The aperture allows the condyle to be seen and palpated through the optimizer to assure proper positioning. For the embodiment shown, the optimizer is fabricated from transparent or translucent plastic to assist in visual alignment and the body incorporates fist indicia 14 demonstrating a range of approximate positioning of the kneecap. An angular zone 16 extends from the lateral condyle aperture to the periphery 18 of the body with a graphic indicator 20 for alignment with the kneecap.

An upper alignment arm 22 extends from the body at a predetermined angle 24 for alignment of the optimizer on the upper leg with second indicia 26 which is employed on a pants seam or similar index for alignment between the knee and the hip. A lower alignment arm 28 depends from the body for positioning of the optimizer on the lower leg with third indicia 30 for alignment with the lateral malleolus ankle bone. For the embodiment shown, the third indicia incorporates a second angular zone 32 for determining a range of proper angle. With the cyclist's foot on the pedal with the pedal at the 6 o'clock to 8 o'clock position (furthest point from the saddle), the upper leg aligns with the upper alignment arm, specifically the second indicia, between the hip and the lateral condyle and the lower leg aligns with the lower alignment arm, specifically the third indicia, between the lateral condyle and lateral malleolus ankle bone upon proper positioning of the sear height.

For the embodiment shown, the second angular zone provided in the third indicia allows positioning through a range of leg angle between approximately 25° and 35° with a medial 30° line 31 from reference axis 33 for central reference. The actual activity undertaken by the cyclist, spinning or road riding as examples, may dictate a different angle for optimum performance and injury prevention. However, the angular range between 25° and 35° has been demonstrated as providing the best performance over multiple uses. The second angular zone includes secondary visual clues such as green bar 34 and red bars 36a and 36b (green and red coloration represented by hatching) for clear indication of proper or improper positioning of the lateral malleolus ankle bone.

For the embodiment shown, the aperture for alignment with the lateral condyle is located at the vertex of the first, second and third alignment indicia providing the basic positioning of the focal point. The alignment indicia are printed or etched of the material of the optimizer and employ coloration or other supplemental aids for clarity in positioning as previously described.

Figure 4:
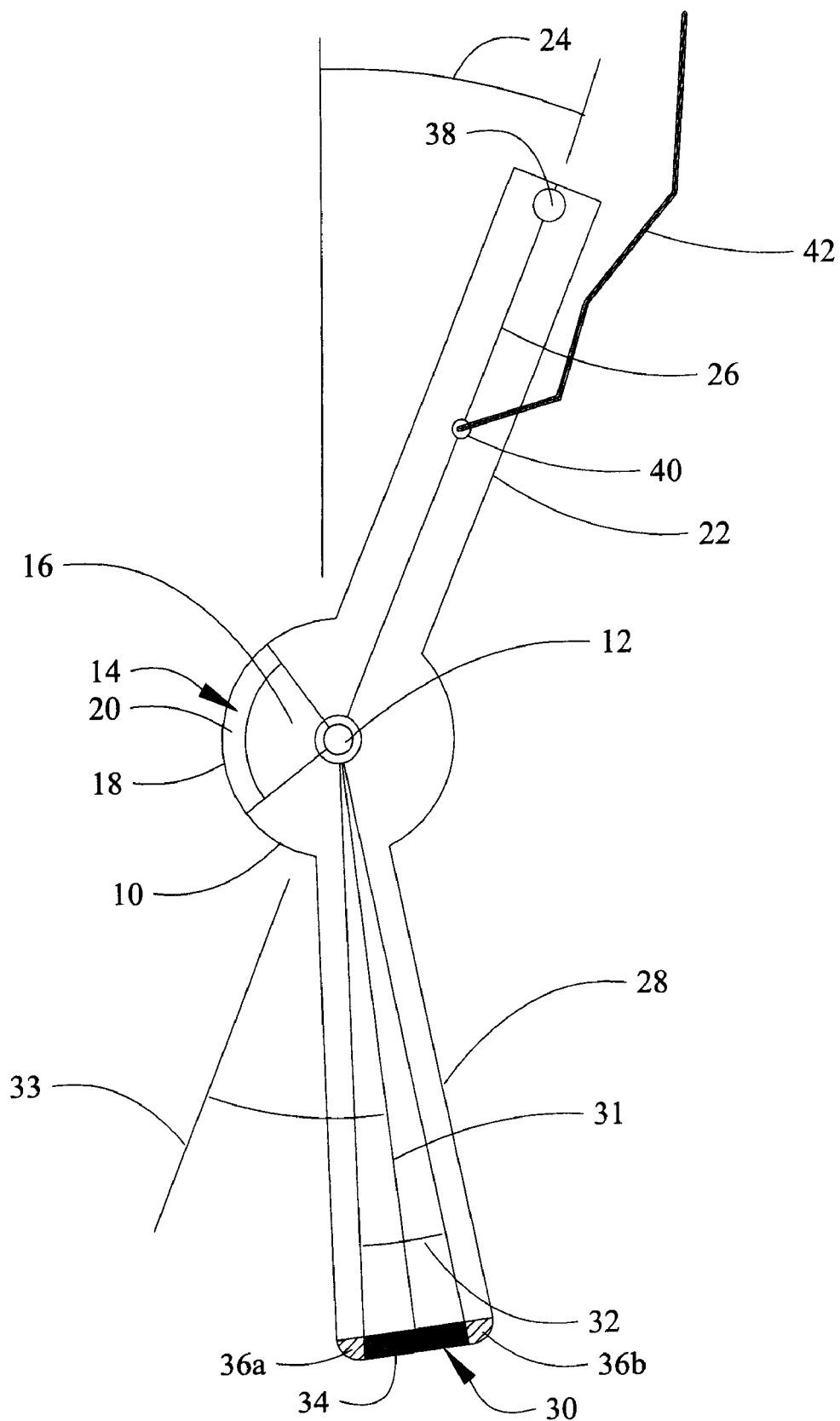
FIG. 4 is a detail side view of a second embodiment of the invention with additional features.
Figure 5:
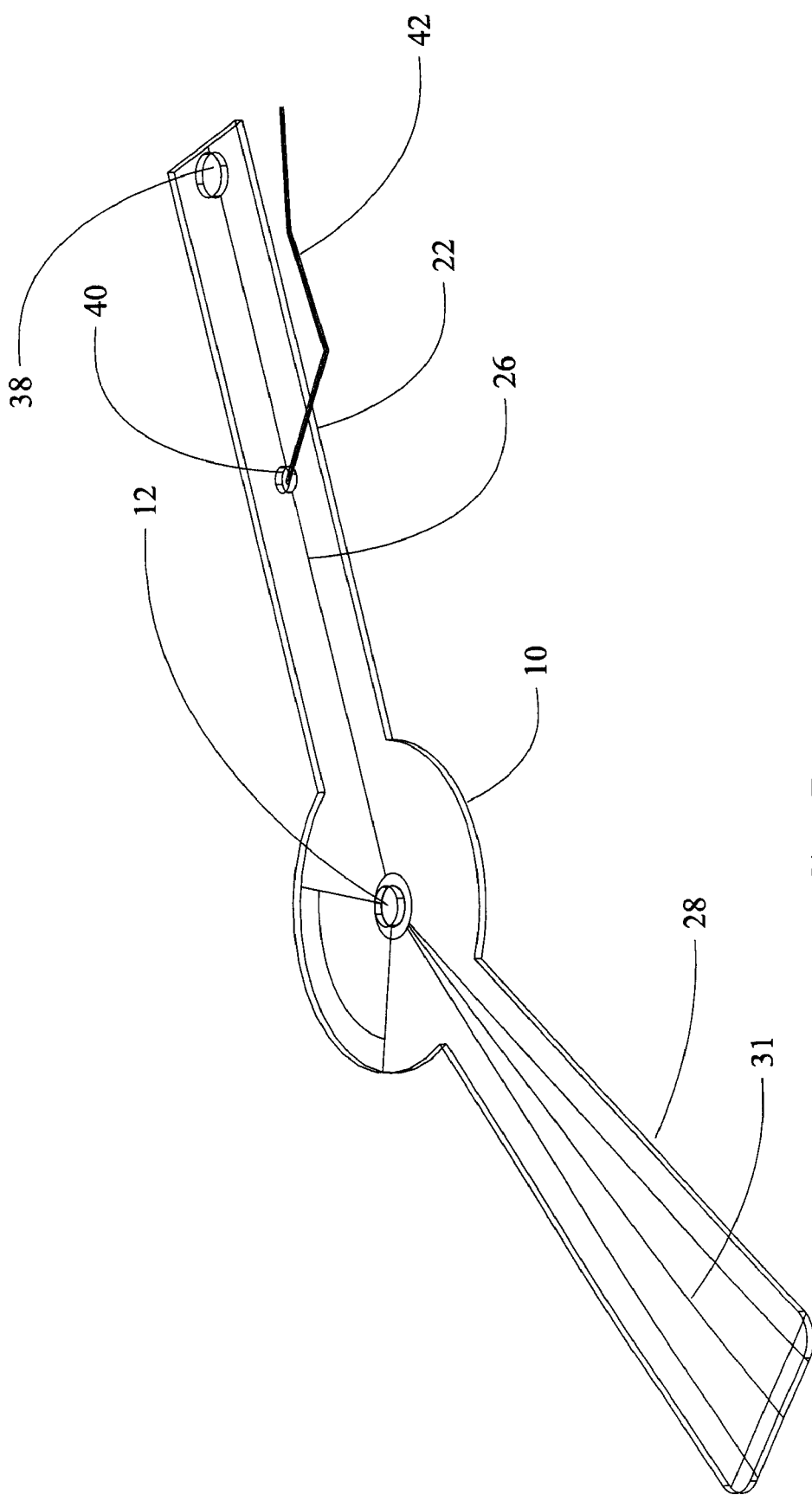
FIG. 5 is an isometric view of the embodiment of FIG. 4 with thickness exaggerated for clarity of presentation.

Additional features of the invention as shown in detail of a second embodiment in FIG. 4 include a second aperture 38 for alignment with the protruding ball of the hip. However, since leg length varies significantly for multiple users to avoid a requirement for a range of sizes of the optimizer, a third aperture allows alignment with the second indicia for accurate positioning of the optimizer on the upper leg. FIG. 5 shows an isometric view of the second embodiment with the thickness exaggerated for clarity.

The optimizer is used for seat adjustment to optimize pedal angle for a cyclist by providing a template having a central body with an aperture, a first alignment arm extending from the central body and having an alignment indicia, and, a second alignment arm extending from the central body at a predetermined angle with respect to the first alignment arm and having an angular alignment indicia.

The aperture is positioned over the lateral condyle in the cyclist's knee using the knee cap indicia on the central body for basic positioning and with the first alignment arm positioned with the alignment indicia extending between the knee and hip of the cyclist. The seat height is then adjusted such that the angular alignment indicia of the second alignment arm is positioned over the malleolus bone of the ankle of the cyclist. For the second embodiment described above, the string extending from the second aperture in the first alignment arm is extended to the hip overlapping the alignment indicia to assure proper positioning of the arm.

Having now described the invention in detail as required by the patent statues, those skilled in the art will recognize modifications and substitutions to the specific embodiments disclosed herein. Such modifications are within the scope and intent of the present invention as defined in the following claims.

What is claimed is:

1. An apparatus for optimizing pedal angle for a cyclist comprising:
   a central body having an aperture for positioning over a lateral condyle in a cyclist's knee;
   a first alignment arm extending from the central body and having an alignment indicia for positioning between the knee and hip of the cyclist and an aperture bisected by the alignment indicia and a string secured in the aperture for alignment along the alignment indicia to the hip; and,
   a second alignment arm extending from the central body at a predetermined angle with respect to the first alignment arm and having an angular alignment indicia for relative placement over a malleolus bone of an ankle of the cyclist.

2. An apparatus as defined in claim 1 wherein the central body further includes an angular indicia for positioning proximate a knee cap on the cyclist's knee.

3. An apparatus for optimizing pedal angle for a cyclist comprising:
   a central body having an aperture for positioning over a lateral condyle in a cyclist's knee;
   a first alignment arm extending from the central body and having an alignment indicia for positioning between the knee and hip of the cyclist; and,
   a second alignment arm extending from the central body at a predetermined angle with respect to the first alignment arm and having an angular alignment indicia for relative placement over a malleolus bone of an ankle of the cyclist including a first secondary visual cue for a first proper range of alignment angle for the malleolus bone and a second set of secondary visual cues for improper angular alignment.

4. An apparatus as defined in claim 3 wherein the angular alignment indicia incorporated in the second alignment arm includes a range of leg angle between approximately 25° and 35° with a medial 30° line.

5. An apparatus as defined in claim 3 wherein the central body further includes an angular indicia for positioning proximate a knee cap on the cyclist's knee.

* * * * *